United States Patent [19]

Janin

[11] 4,182,873

[45] Jan. 8, 1980

[54] PROCESS FOR THE PREPARATION OF THIAZOLESULPHENAMIDES

[75] Inventor: Raymond Janin, Carmagnac-Irigny, France

[73] Assignee: Rhone-Poulenc S.A., Paris, France

[21] Appl. No.: 582,983

[22] Filed: Jun. 2, 1975

Related U.S. Application Data

[63] Continuation-in-part of Ser. No. 402,914, Oct. 2, 1973, abandoned, and Ser. No. 415,307, Nov. 13, 1973, abandoned.

[51] Int. Cl.$^2$ .......................................... C07D 277/78
[52] U.S. Cl. ................................. 544/133; 548/167; 548/168; 544/135; 544/136; 548/183; 548/189
[58] Field of Search ................. 260/306.6 A, 302 SN, 260/247.1 L, 247.1 H; 544/133, 135, 136

[56] References Cited

U.S. PATENT DOCUMENTS 3,737,431   6/1973   Campbell et al. ............ 260/306.6 A

FOREIGN PATENT DOCUMENTS 805635   3/1974   Belgium .
807204   5/1974   Belgium .

Primary Examiner—Nicholas S. Rizzo
Attorney, Agent, or Firm—Stevens, Davis, Miller & Mosher

[57] ABSTRACT

Thiazolesulphenamides, useful as rubber vulcanization accelerators, are made by reaction of a 2-mercaptothiazole or a 2,2'-dithiazolyl disulphide with ammonia or a primary or secondary amine in the presence of oxygen and a copper catalyst of specified kind.

13 Claims, No Drawings

PROCESS FOR THE PREPARATION OF THIAZOLESULPHENAMIDES

This application is a continuation-in-part of my prior applications Ser. Nos. 402,914, filed Oct. 2, 1973, and 415,307, filed Nov. 13, 1973, both now abandoned.

The present invention relates to the preparation of thiazolesulphenamides, especially benzothiazolesulphenamides, by oxidising condensation of a 2-mercapto-thiazole or a 2,2'-dithiazolyl disulphide with ammonia or a primary or secondary amine.

Thiazolesulphenamides, and especially benzothiazolesulphenamides, are important industrial products used in the rubber industry as vulcanisation accelerators. Their value has prompted numerous investigations to improve the processes for their preparation and to develop new processes. Examples of known methods for the preparation of thiazolesulphenamides include: the reaction of a 2-mercapto-thiazole with a chloramine in an alkaline medium (or of a preformed alkali metal thiazolethiolate with a chloramine); the reaction of a thiazylsulphenyl halide (particularly a chloride) with excess of an amine; and the oxidising condensation of a 2-mercapto-thiazole with an amine in the presence of an oxidising agent which can be hydrogen peroxide, a persulphate, a ferricyanide, a halogen, or an alkali metal hypochlorite. The last method, which makes use of an alkali metal hypochlorite as oxidising agent, is the one most used in industry because it gives excellent yields of sulphenamides. However, this process has the disadvantage of consuming alkali metal hypochlorites in considerable quantities.

Starting from the 2,2'-diathiazolyl disulphides, the most common method consists of condensing them with primary or secondary amines in an aqueous or organic medium preferably in the presence of an oxidising agent such as an alkali metal hypohalite (for example, sodium hypochlorite), a halogen, (e.g. chlorine or bromine), hydrogen peroxide, an alkali metal persulphate (e.g. potassium persulphate) or an alkali metal ferricyanide. Alkali metal hypochlorites are used most frequently. Although these processes give good yields of thiazolesulphenamides, they have the disadvantage of consuming considerable amounts of expensive oxidising agents. In an alternative process dithiazolyl disulphides are condensed with N-chloramines in the presence of a stoichiometric amount of free amine acting as a hydrochloric acid acceptor. However, this reaction still involves the consumption of chlorine to prepare the N-chloroamines and has another disadvantage in that the amine used must be liberated from its hydrochloride before it is recycled.

In order to make the oxidising condensation more economical, means have been sought for employing other oxidising agents, and especially oxygen as such or in admixture with inert gases, e.g. air. Thus, Canadian Patent No. 863,351 has proposed a process for the preparation of benzothiazolesulphenamides by reacting an amine with 2-mercapto-benzothiazole (or one of its alkali metal salts) or with bis-(2,2-benzothiazolyl) disulphide in the presence of oxygen or air and a metal phthalocyanine possessing, where necessary, a hydrophilic group such as a sulphonate group as the catalyst. The metal phthalocyanine may be of manganese, vanadium, chromium, nickel, iron or copper, that of cobalt being preferred. Metal compounds such as ferrous acetate, ferric chloride, chromium chloride, nickel acetate or cobalt acetate do not make it possible to produce benzothiazolesulphenamides by reaction of mercaptobenzothiazole with an amine, in the presence of oxygen or air, which demonstrates the specific behaviour of the phthalocyanines in this type of reaction.

It has now been found that, in contrast to what happens with other transition metal derivatives, it is possible to prepare thiazolesulphenamides by condensation of a 2-mercapto-thiazole or a 2,2'-dithiazolyl disulphide with ammonia or a primary or secondary amine in the presence of oxygen as the oxidising agent, and of, as catalyst, copper, copper oxide, a salt of copper with an inorganic acid, a carboxylic acid, or a sulphonic acid, or a copper β-diketonate chelate.

More specifically, the present invention provides a process for the preparation of thiazolesulphenamides of the formula:

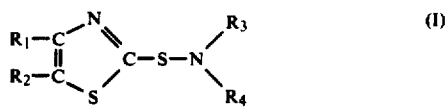

in which $R_1$ and $R_2$, which may be identical or different, are each hydrogen, halogen, alkyl of 1 to 5 carbon atoms, alkoxy of 1 to 5 carbon atoms, or aryl of 6 to 12 carbon atoms, the said aryl being unsubstituted or substituted by one or more halogen atoms, nitro groups, alkyl radicals of 1 to 5 carbon atoms, or alkoxy radicals of 1 to 5 carbon atoms, or $R_1$ and $R_2$ together form a divalent radical of the formula:

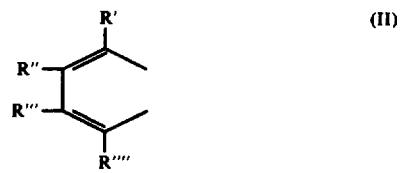

in which R', R'', R''' and R'''', which may be identical or different, are each hydrogen, halogen, nitro, alkyl of 1 to 5 carbon atoms, alkoxy of 1 to 5 carbon atoms or aryl of 6 to 12 carbon atoms, and $R_3$ and $R_4$, which may be identical or different, are each hydrogen, straight or branched alkyl of 1 to 20 carbon atoms, cycloalkyl of 5 to 12 carbon atoms, or aralkyl of 7 to 15 carbon atoms, or together with the nitrogen atom to which they are bonded, form a heterocyclic ring of 5 to 7 ring atoms and 1 to 3 hetero-atoms chosen from nitrogen, oxygen and sulphur, the said ring being unsubstituted or substituted by alkyl of 1 to 5 carbon atoms or alkoxy of 1 to 5 carbon atoms, by reacting a mercapto-thiazole of the formula:

or a 2,2'-dithiazolyl disulphide of the formula:

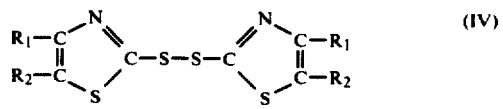

with a compound of the formula:

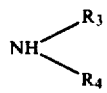

in which $R_1$, $R_2$, $R_3$ and $R_4$ have the meanings given above, in the presence of oxygen and copper or a copper compound as aforesaid as catalyst.

In the above formulae, $R_1$, $R_2$, $R'$, $R''$, $R'''$ and $R''''$ represent, more particularly, chlorine, bromine, methyl, ethyl, n-propyl, isopropyl, n-, iso-, sec- or t-butyl, n- or iso-pentyl, methoxy, ethoxy, n-propoxy, isopropoxy, or n-, iso-, sec- or t-butoxy, toluyl, ethylphenyl, nitrophenyl, chlorophenyl, or naphthyl; and $R_3$ and $R_4$ represent especially methyl, ethyl, propyl, iso-propyl, n-butyl, isobutyl, sec-butyl, t.-butyl, n-pentyl, iso-pentyl, n-hexyl, n-heptyl, n-octyl, n-decyl, cyclopentyl, cyclohexyl, 2-methyl-cyclohexyl, cycloheptyl, cyclooctyl, cyclododecyl, benzyl or β-phenyl-ethyl, or, together with the nitrogen atom to which they are bonded, form a 1-piperidiyl, 4-morpholyl, 1-pyrrolidyl, 4-alkyl-1-piperazinyl, 3,5-dimethyl-4-morpholyl, 2,6-dimethyl-4-morpholyl, 2-methyl-5-ethyl-1-piperidyl or 1-hexahydroazepinyl radical.

Specific examples of 2-mercapto-thiazoles of formula III which can be used to prepare the sulphenamides of formula (I), are:
2-Mercapto-thiazole
2-mercapto-4-methyl-thiazole
2-mercapto-4-ethyl-thiazole
2-mercapto-4-n-propyl-thiazole
2-mercapto-4-n-butyl-thiazole
2-mercapto-4,5-dimethyl-thiazole
2-mercapto-4,5-di-n-butyl-thiazole
2-mercapto-4-phenyl-thiazole
2-mercapto-benzothiazole
2-mercapto-4-methyl-benzothiazole
2-mercapto-5-methyl-benzothiazole
2-mercapto-6-methyl-benzothiazole
2-mercapto-4,5-dimethyl-benzothiazole
2-mercapto-4-phenyl-benzothiazole
2-mercapto-4-methoxy-benzothiazole
2-mercapto-6-methoxy-benzothiazole
2-mercapto-5,6-dimethoxy-benzothiazole
2-mercapto-6-methoxy-4-nitro-benzothiazole
2-mercapto-6-ethoxy-benzothiazole
2-mercapto-4-chloro-benzothiazole
2-mercapto-5-chloro-benzothiazole
2-mercapto-7-chloro-benzothiazole
2-mercapto-5-chloro-6-methoxy-benzothiazole
2-mercapto-5-chloro-4-nitro-benzothiazole
2-mercapto-5-chloro-6-nitro-benzothiazole
2-mercapto-4,5-dichloro-benzothiazole
2-mercapto-4,7-dichloro-benzothiazole and
2-mercapto-5-nitro-benzothiazole.

Specific examples of 2,2'-dithiazolyl disulphides of formula IV which can be used to prepare the sulphenamides of the formula (I) are:
2,2'-dithiazolyl disulphide
2,2'-bis-(4-methyl-thiazolyl) disulphide
2,2'-bis-(4-ethyl-thiazolyl) disulphide
2,2'-bis-(4-phenyl-thiazolyl) disulphide
2,2'-bis-(4-p-bromophenyl-thiazolyl) disulphide
2,2'-bis-(4-m-chlorophenyl-thiazolyl) disulphide
2,2'-bis-(4-m-nitrophenyl-thiazolyl) disulphide
2,2'-bis-(5-chloro-4-phenyl-thiazolyl) disulphide
2,2'-dibenzothiazolyl disulphide
2,2'-bis-(6-methyl-benzothiazolyl) disulphide
2,2'-bis-(4-methyl-benzothiazolyl) disulphide
2,2'-bis-(4-methoxy-benzothiazolyl) disulphide
2,2'-bis-(6-ethoxy-benzothiazolyl) disulphide
2,2'-bis-(5-chloro-benzothiazolyl) disulphide
2,2'-bis-(5-chloro-4-nitro-benzothiazolyl) disulphide
2,2'-bis-(5-chloro-6-nitro-benzothiazolyl) disulphide
2,2'-bis-(6-nitro-benzothiazolyl) disulphide.

The 2-mercapto-benzothiazoles and 2,2'-dibenzothiazolyl disulphides, i.e. compounds in which $R_1$ and $R_2$ together form a radical of formula —CH=CH-CH=CH—, form a preferred class of starting materials.

Examples of suitable compounds of formula V are: ammonia; methylamine, ethylamine, n-propylamine, isopropylamine, n-butylamine, sec.-butylamine, t-butylamine, n-pentylamine, isopentylamine, t-pentylamine, n-hexylamine, t-octylamine, n-octylamine, cyclopentylamine, cyclohexylamine, 2-methyl-cyclohexylamine, (cyclopentylmethyl)-amine, benzylamine, α-methyl-benzylamine, dimethylamine, diethylamine, di-n-propylamine, di-iso-propylamine, di-n-butylamine, di-t-butylamine, di-n-pentylamine, di-isopentylamine, dicyclohexylamine, ethylcyclohexylamine, methyl-n-butylamine, methylbenzylamine, piperidine, morpholine, pyrrolidine, 2,6-dimethylmorpholine, 3,5-dimethylmorpholine, hexahydroazepine, N-methylpiperazine, N-ethylpiperazine, thiomorpholine and 2-methyl-5-ethyl-piperidine.

Specific examples of thiazolesulphenamides which can be produced by the process of the invention are:
Thiazolesulphenamide
N-isopropyl-thiazolesulphenamide
4,5-dimethyl-thiazolesulphenamide
N-t-butyl-4-methyl-thiazolesulphenamide
N-cyclohexyl-4-methyl-thiazolesulphenamide
N,N-diethyl-4-methyl-thiazolesulphenamide
N-isopropyl-4-methyl-thiazolesulphenamide
N-isopropyl-4,5-dimethyl-thiazolesulphenamide
N,N-dicyclohexyl-4-phenyl-thiazolesulphenamide
N,N-dicyclopentyl-4-phenyl-thiazolesulphenamide
N,N-diethyl-thiazolesulphenamide
N,N-diethyl-4,5-dimethyl-thiazolesulphenamide
N,N-dimethyl-4-ethyl-thiazolesulphenamide
N,N,4,5-tetramethyl-thiazolesulphenamide
N,N,4-triethyl-thiazolesulphenamide
N-sec-butyl-4,5-dimethyl-thiazolesulphenamide
N-cyclohexyl-thiazolesulphenamide
N-cyclohexyl-4,5-dimethyl-thiazolesulphenamide
N-cyclohexyl-4-ethyl-thiazolesulphenamide
N,N-di-n-pentyl-4,5-dimethyl-thiazolesulphenamide
benzothiazolesulphenamide
N-methyl-benzothiazolesulphenamide
N,N-dimethyl-benzothiazolesulphenamide
N-ethyl-benzothiazolesulphenamide
N,N-diethyl-benzothiazolesulphenamide
N-cyclohexyl-benzothiazolesulphenamide
N,N-dicyclohexyl-benzothiazolesulphenamide
N-cyclopentyl-benzothiazolesulphenamide
N,N-di-n-butyl-benzothiazolesulphenamide
N-n-propyl-benzothiazolesulphenamide
N-isopropyl-benzothiazolesulphenamide
N,N-di-isopropyl-benzothiazolesulphenamide
N-α-methylbenzyl-benzothiazolesulphenamide
N-(t.octyl)-benzothiazolesulphenamide
N-benzyl-benzothiazolesulphenamide
N-methyl-N-cyclohexyl-benzothiazolesulphenamide
N-ethyl-N-cyclohexyl-benzothiazolesulphenamide N-cyclohexyl-6-nitro-benzothiazlesulphenamide
N-n-butyl-benzothiazolesulphenamide
N-t-butyl-benzothiazolesulphenamide
N-sec-butyl-benzothiazolesulphenamide
N-4-morpholinyl-benzothiazolesulphenamide
N-(2,6-dimethyl-4-morpholinyl)benzothiazolesulphenamide
N-(3,5-dimethyl-4-morpholinyl)-benzothiazolesulphenamide
N-1-piperidinyl-benzothiazolesulphenamide
N-1-pyrrolidinyl-benzothiazolesulphenamide, and
N-1-hexahydroazepinyl-benzothiazolesulphenamide.

When copper metal is used as catalyst, it is preferably in the form of a powder. However, although copper metal is an adequate catalyst, it is preferable to use copper oxide, a salt of copper with an inorganic acid, a carboxylic acid or a sulphonic acid or a copper β-diketonate chelate. In this case, the oxidation level of the metal is not critical, nor is the nature of the radical which accompanies it. For practical reasons, however, it is preferable to choose a compound which is soluble in the reaction medium used, which can be aqueous, organic or aqueous organic. Examples of suitable catalysts are: copper oxides ($Cu_2O$ and $CuO$); copper salts of inorganic acids, such as the halides (cuprous or cupric chloride and cuprous or cupric bromide), copper sulphides ($Cu_2S$ and $CuS$), copper thiosulphates ($Cu_2H_4[S_2O_3]_3$), copper sulphites ($Cu_2SO_3.H_2O$ and $Cu[Cu(SO_3)]_2.2H_2O$), neutral cuprous and cupric sulphates ($Cu_2SO_4$; $CuSO_4.H_2O$; $CuSO_4.3H_2O$ and $CuSO_4.5H_2O$), basic copper sulphates of the formula $SO_3.4CuO.nH_2O$, cuprous and cupric nitrates, cuprous and cupric phosphates, copper borates, copper cyanides, copper cuprocyanide ($Cu[Cu(CN)_2]_2.5H_2O$) and copper thiocyanates; double salts of copper and alkali or alkaline earth metals (for example, $K_2[CuCl_3]$ and $K[CuCl_2].H_2O$); and salts of copper with aliphatic, cycloaliphatic, arylaliphatic and aromatic monocarboxylic or polycarboxylic acids, optionally substituted by a halogen atom or one or more functional groups such as hydroxyl, thiol, nitro, nitrile and aldehyde groups, e.g. formic, acetic, chloroacetic, dichloroacetic, propionic, butyric, caproic, valeric, octanoic, decanoic, oxalic, adipic, tartaric, cyclohexanecarboxylic, naphthenic, benzoic, phthalic, naphthoic and salicyclic acids.

Specific examples of suitable copper salts of carboxylic acids are: cuprous and cupric acetates ($Cu[CH_3COO]$ and $Cu[CH_3COO]_2.H_2O$), cupric formate, basic copper acetates ($2Cu[CH_3COO]_2.Cu(OH)_2.5H_2O$; $Cu[CH_3COO]_2.Cu(OH)_2.5H_2O$; $Cu[CH_3COO]_2.-2Cu(OH)_2$ and $Cu[CH_3COO]_2.3Cu(OH)_2.2H_2O$), basic copper formates ($Cu[HCOO]_2.3Cu(OH)_2$ and $Cu[HCOO]_2.2Cu(OH)_2$), copper propionates, butyrates, pentanoates, and octanoates, copper oxalates and copper resinates, naphthenates, benzenecarboxylates and salicylates.

Another useful class of catalyst are the copper salts of alkyl-, cycloalkyl-, aralkyl and aryl-mono- or poly-sulphonic acids such as methane-sulphonic, ethane-sulphonic, ethane-disulphonic, benzene-sulphonic, toluene-sulphonic and naphthalene-sulphonic acids.

Another group of copper catalysts which can be employed in the process of the invention is formed by the β-diketonate chelates of copper with β-diketones such as acetyl-acetone (pentane-2,4-dione), hexane-2,4-dione, heptane-2,4-dione, 5-methyl-hexane-2,4-dione, octane-2,4-dione, 3-methoxy-pentane-2,4-dione, heptane-3,5-dione, 1,1,1-trifluoro-pentane-2,4-dione, benzoylacetone, dibenzoyl-methane, o-methoxy-benzoyl-acetone, 1,1,1-trifluoro-2-benzoyl-acetone, β-naphthoyl-trifluoro-acetone, 3-methyl-pentane-2,4-dione, 3-butyl-pentane-2,4-dione, cyclopentane-1,3-dione, cyclohexane-1,3-dione, 5,5-dimethylcyclohexane-1,3-dione (dimedone), 2-acetylcyclohexanone, hexahydronaphthalene-1,8-dione and 1-hydroxy-benzoylacetone. Examples of copper compounds of this group are bis-(pentane-2,4-dionato)-copper, bis-(3-bromo-pentane-2,4-dionato)-copper, bis-(3-chloro-pentane-2,4-dionato)-copper, bis-[1-chloro-1,1-difluoro-pentane-2,4-dionato]-copper, bis-(1,1,1-trifluoro-pentane-2,4-dionato)-copper, bis-(3-ethyl-pentane-2,4-dionato)-copper, bis-(3-methyl-pentane-2,4-dionato)-copper, bis-(3-methyl-1-phenyl-pentane-2,4-dionato)-copper, bis-(3-benzyl-pentane-2,4-dionato)-copper, bis-(3-butyl-pentane-2,4-dionato)-copper, bis-(1-methoxy-3-methyl-pentane-2,4-dionato)-copper, bis-(3-methoxy-pentane-2,4-dionato)-copper, bis-(hexane-2,4-dionato)-copper, bis-(5,5-dimethyl-hexane-2,4-dionato)-copper, bis-(2,2-dimethyl-heptane-3,5-dionato)-copper, bis-(5-ethyl-decane-4,6-dionato)-copper, bis-(3-ethyl-heptane-2,4-dionato)-copper, bis-(3-acetyl-cyclopentane-2,4-dionato)-copper, bis-(cyclohexane-1,3-dionato)-copper, bis-(5,5-dimethyl-cyclohexane-1,3-dionato)-copper, bis-(cyclodecane-1,3-dionato)-copper, bis-(cycloundecane-1,3-dionato)-copper and bis-(cyclododecane-1,3-dionato)-copper.

Copper salts of inorganic acids or of saturated aliphatic carboxylic acids (or their mixtures) containing 1 to 20 carbon atoms or β-diketonates, and especially copper acetylacetonates, form a class of catalyst which possesses a considerable advantage compared with metal phthalocyanines containing hydrophilic groups, the use of which is recommended in Canadian Pat. No. 863,351, because they are common compounds which are easy to prepare.

The molar ratio of ammonia or amine to the mercapto-thiazole or 2,2'-dithiazolyl disulphide can vary within quite wide limits depending on the reaction conditions; when the latter is carried out in water or in an organic solvent, it is possible to employ amounts of reagents close to the stoichiometric requirements, the molar ratio being then approximately 1 in the case of the mercapto compounds or approximately 2 in the case of the disulphides, although it is preferred to use an excess of the ammonia or amine which is 0.5 to 5 times the stoichiometric amount. In the case of amines, it is advantageous to employ them as the solvent for the reaction.

Suitable organic solvents for carrying out the condensation of the mercapto-thiazoles or disulphides and the ammonia or amine, include aliphatic alcohols (e.g. methanol, ethanol, n- and iso-propanol and t-butanol); amides such as dimethylformamide and dimethylacetamide; nitriles such as acetonitrile; esters such as methyl acetate and ethyl acetate; tertiary amines such as trimethylamine and triethylamine; tertiary heterocyclic bases such as pyridine; and aromatic hydrocarbons such as benzene and toluene.

The amount of copper employed, expressed as the ratio of the number of gram atoms of copper to the number of mols of 2-mercapto-thiazole or 2,2'-dithiazolyl disulphide, can vary within quite wide limits, but is generally between 0.0001 and 0.5, and preferably between 0.001 and 0.1.

The reaction is carried out at temperatures of between 0° and 200° C., and preferably between 20° and 150° C., and the oxygen pressure may be between 0.1 and 30 bars.

It is simple to carry out the process of the invention because all that is necessary is to bring the liquid reagents containing the catalyst into contact with oxygen, or a gas containing oxygen, in accordance with the usual techniques for carrying out reactions between a liquid phase and a gas phase, and to stop the reaction when approximately the theoretical amount of oxygen has been abosrbed. The process is very suitable for continuous operation.

The following Examples illustrate the invention.

EXAMPLE 1

30.5 g. of cyclohexylamine, 5.16 g. of 2-mercapto-benzothiazole and 200 mg of cupric acetate dihydrate are introduced into a 200 cm$^3$ cylindrical glass reactor which possesses a double jacket through which a hot liquid can flow and which is equipped with a thermometer, a reflux condenser, a gas inlet and a stirring system. The mixture is stirred until dissolution has taken place, the apparatus is purged with oxygen and the contents of the flask are heated to 75° C. The flask is then connected to an oxygen vessel and these conditions are maintained for 1 hour 6 minutes, during which time 280 cm$^3$ of oxygen are absorbed.

The contents of the flask are cooled to 20° C. and the cyclohexylamine is then determined by potentiometry (34.5 mmols were converted). It is also found, by thin layer chromatographic analysis carried out on a sample of the reaction mixture, that all the 2-mercapto-benzothiazole has been converted. The contents of the flask are then diluted with twice their volume of water so as to precipitate N-cyclohexyl-benzothiazolesulphenamide which is filtered off, washed on the filter with distilled water, drained and dried to constant weight in an oven in vacuo. In this way, 6.8 g. of a product containing 98.9% of N-cyclohexyl-benzothiazolesulphenamide and 1.1% of cyclohexylamine are obtained. Taking into account the benzothiazolesulphenamide dissolved in the filtrate, a total of 29.5 mmols of the desired product are formed, which corresponds to the following yields: 98% relative to the 2-mercapto-benzothiazole employed and to the oxygen absorbed, and 85% relative to the cyclohexylamine converted. The yields of precipitated sulphenamide are respectively 86% and 75%.

EXAMPLE 2

The procedure of Example 1 is followed at 25° C. and at 50° C., the duration of oxygen absorption being respectively 1 hour 40 minutes and 1 hour 45 minutes. The yields of precipitated sulphenamide relative to the 2-mercapto-benzothiazole employed are as follows: at 25° C.: 40%; and at 50° C.: 69%.

EXAMPLE 3

The procedure of Example 1 is followed at 50° C. and with an amount of copper acetate corresponding to 1 mmol per 50 mmols of 2-mercapto-benzothiazole. The duration of oxygen absorption is 2 hours 45 minutes. The yield of precipitated sulphenamide is 71% relative to the 2-mercapto-benzothiazole converted.

EXAMPLE 4

The procedure of Example 1 is followed at 50° C., replacing the cyclohexylamine by morpholine. The corresponding sulphenamide is obtained in a yield of precipitated product of 86% relative to the 2-mercapto-benzothiazole. The duration of the reaction is 4 hours 20 minutes, after which time the theoretical amount of oxygen has been absorbed.

EXAMPLES 5 to 13

The procedure of Example 1 is followed, but at 50° C. and replacing the copper acetate by various copper derivatives. The results listed in the following table are obtained, in which the yields are expressed as precipitated sulphenamide relative to the 2-mercapto-benzothiazole introduced.

| Ex. | Catalyst | Duration | Yeild |
|---|---|---|---|
| 5 | Cupric nitrate | 2 hrs. 50 mins. | 77% |
| 6 | Cupric iodide | 6 hrs. 05 mins. | 82% |
| 7 | Cupric cyanide | 3 hrs. 50 mins. | 70% |
| 8 | Cupric acetyl-acetonate | 3 hrs. 30 mins. | 60% |
| 9 | Cuprous oxide | 6 hrs. 45 mins. | 75% |
| 10 | Cupric sulphate | 5 hrs. 45 mins. | 75% |
| 11 | Cuprous chloride | 5 hrs. | 75% |
| 12 | Cupric chloride | 3 hrs. | 80% |
| 13 | Copper | 4 hrs. 15 mins. | 72% |

EXAMPLES 14 to 18

The technique of Example 1 is followed, in the presence of a co-solvent, under the following conditions:
Temperature: 50° C.
Cu/2-mercapto-benzothiazole ratio: 1/30
Cyclohexylamine/2-mercapto-benzothiazole molar ratio: 5
Cyclohexylamine/co-solvent volume ratio: 1
The following results are obtained:

| EX. | Co-solvent | Duration | Yeild (1) |
|---|---|---|---|
| 14 | Water | 2 hrs. 15 mins. | 82% |
| 15 | Dimethylformamide | 2 hrs. 20 mins. | 81% |
| 16 | Ethanol | 6 hrs. 30 mins. | 60% |
| 17 | Triethylamine | 3 hrs. 10 mins. | 85% |
| 18 | Dimethylsulphoxide | 3 hrs. 30 mins. | 86.1% |

(1) The yields are expressed as in Examples 5 to 13.

EXAMPLE 19

The procedure of Example 1 is followed, but at 25° C. and introducing the following amounts of reagents:
2-Mercapto-benzothiazole: 5.15 g
96.3% by weight pure t.-butylamine: 24.80 g and cupric acetate: 0.200 g.

Absorption of oxygen is continued for 6 hours 20 minutes at 25° C., after which time 270 cm$^3$ of oxygen have been absorbed. The thick, heterogeneous reaction mixture thus obtained is cooled to 20° C. and then diluted by adding 70 cm$^3$ of distilled water. The mixture is stirred for 20 minutes and the solid in suspension is then filtered off. In this way, 5.03 g of a product are obtained which, after drying to constant weight at 50° C. under reduced pressure, has a melting point of 109° C. and contains 91% of N-(t.-butyl)benzothiazolesulphenamide, identified by thin layer chromatography, and measured by decomposition using H$_2$S and measuring the amine liberated with N/2 HCl. The yield is 62.5% relative to the 2-mercapto-benzothiazole employed.

EXAMPLE 20

37 cm³ of cyclohexylamine (0.288 mol), 5.25 g. of 2,2'-dibenzylthiazolyl disulphide (0.015 mol) and 0.205 g. of cupric acetate are introduced into a 200 cm³ glass reactor equipped with a double jacket for the circulation of a heating liquid, a thermometer, a reflux condenser and a stirring system. The apparatus is connected to a source of oxygen via the condenser and the contents are then heated to 50° C. The contents of the reactor are kept under these conditions for 25 minutes and are then cooled to 20° C. and the apparatus is purged with nitrogen. A total of 190 cm³ of oxygen (0.007 mol) is absorbed. The excess cyclohexylamine is measured with N $H_2SO_4$ and it is found that 0.266 mol remain. 70 cm³ of distilled water are added to the reaction mixture and the whole is stirred for 20 minutes at 20° C. A precipitate is obtained which is filtered off, washed on the filter twice with 20 cm³ of water, and then dried in an oven to constant weight. In this way, 6.17 g. of a white product, m.p. (Koffler bench) 102°–103° C., are obtained, containing 91.5% of N-cyclohexyl-benzothiazole-sulphenamide (measured by dissolving a sample in a 40/60 by volume mixture of toluene and isopropanol, decomposing it with $H_2S$ and measuring the amine liberated by acidimetry). The yield of sulphenamide relative to the disulphide employed is 71.5%.

I claim:

1. In a process for the preparation of a thiazolesulphenamide of the formula:

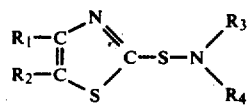

in which $R_1$ and $R_2$, which may be identical or different, are each hydrogen, halogen, alkyl of 1 to 5 carbon atoms, alkoxy of 1 to 5 carbon atoms, or aryl of 6 to 12 carbon atoms, or together form a divalent radical of the formula:

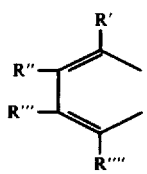

in which R', R", R'" and R"", which may be identical or different, are each hydrogen, halogen, nitro, alkyl of 1 to 5 carbon atoms, alkoxy of 1 to 5 carbon atoms, or aryl of 6 to 12 carbon atoms, and $R_3$ and $R_4$, which may be identical or different, are each hydrogen atoms, a straight or branched alkyl of 1 to 20 carbon atoms, cycloalkyl of 5 to 12 carbon atoms, or aralkyl of 7 to 15 carbon atoms, or, together with the nitrogen atom to which they are bonded, form a heterocyclic ring of 5 to 7 ring atoms of which 1 to 3 are hetero-atoms chosen from nitrogen, oxygen and sulphur and the remainder are carbon atoms, the said ring being unsubstituted or substituted by alkyl of 1 to 5 carbon atoms or alkoxy of 1 to 5 carbon atoms, by condensing a 2-mercapto-thiazole of the formula:

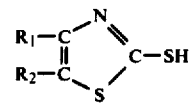

or a 2,2'-dithiazolyl disulphide of the formula:

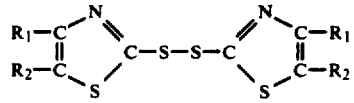

with a compound of the formula:

$R_1$, $R_2$, $R_3$ and $R_4$ having the meanings given above, in the presence of oxygen and a catalyst, the improvement which consists in using, as catalyst, copper, copper oxide, a salt of copper with an inorganic acid, a carboxylic acid, or a sulphonic acid, or a copper β-diketonate chelate.

2. The improvement of claim 1, in which the molar ratio of the compound of formula V to the 2-mercaptothiazole is at least 1:1.

3. The improvement of claim 1, in which the molar ratio of the compound of formula V to the 2,2'-dithiazolyl disulphide is at least 2:1.

4. In a process according to claim 1 for the preparation of a thiazolesulphenamide of the formula:

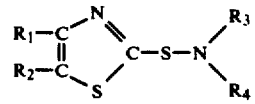

in which $R_1$ and $R_2$, which may be identical or different, are each hydrogen, halogen, alkyl of 1 to 5 carbon atoms, alkoxy of 1 to 5 carbon atoms, or aryl of 6 to 12 carbon atoms, or together form a divalent radical of the formula:

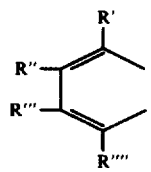

in which R', R", R'" and R"", which may be identical or different, are each hydrogen, halogen, nitro, alkyl of 1 to 5 carbon atoms, alkoxy of 1 to 5 carbon atoms, or aryl of 6 to 12 carbon atoms, and $R_3$ and $R_4$, which may be identical or different, are each hydrogen atoms, a straight or branched alkyl of 1 to 20 carbon atoms, cycloalkyl of 5 to 12 carbon atoms, or aralkyl of 7 to 15 carbon atoms, or, together with the nitrogen atom to which they are bonded, form a heterocyclic ring of 5 to 7 ring atoms of which 1 to 3 are heteroatoms chosen from nitrogen, oxygen and sulphur and the remainder are carbon atoms, the said ring being unsubstituted or substituted by alkyl of 1 to 5 carbon atoms or alkoxy of 1 to 5 carbon atoms, by condensing a 2-mercapto-thiazole of the formula:

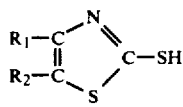
(III)

with a compound of the formula:

(V)

$R_1$, $R_2$, $R_3$ and $R_4$ having the meanings given above, in the presence of oxygen and a catalyst, the improvement which consists in using, as catalyst, copper, copper oxide, a salt of copper with an inorganic acid, a carboxylic acid, or a sulphonic acid, or a copper β-diketonate chelate.

5. In a process according to claim 1 for the preparation of a thiazolesulphenamide of the formula:

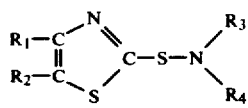
(I)

in which $R_1$ and $R_2$, which may be identical or different, are each hydrogen, halogen, alkyl of 1 to 5 carbon atoms, alkoxy of 1 to 5 carbon atoms, or aryl of 6 to 12 carbon atoms, or together form a divalent radical of the formula:

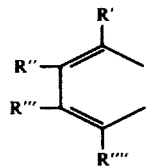
(II)

in which R', R", R'" and R"", which may be identical or different, are each hydrogen, halogen, nitro, alkyl of 1 to 5 carbon atoms, alkoxy of 1 to 5 carbon atoms, or aryl of 6 to 12 carbon atoms, and $R_3$ and $R_4$, which may be identical or different, are each hydrogen atoms, a straight or branched alkyl of 1 to 20 carbon atoms, cycloalkyl of 5 to 12 carbon atoms, or aralkyl of 7 to 15 carbon atoms, or, together with the nitrogen atom to which they are bonded, form a heterocyclic ring of 5 to 7 ring atoms of which 1 to 3 are hetero-atoms chosen from nitrogen, oxygen and sulphur and the remainder are carbon atoms, the said ring being unsubstituted or substituted by alkyl of 1 to 5 carbon atoms or alkoxy of 1 to 5 carbon atoms, by condensing a 2,2'-dithiazolyl disulphide of the formula:

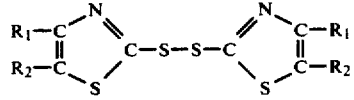
(IV)

with a compound of the formula:

(V)

$R_1$, $R_2$, $R_3$ and $R_4$ having the meanings given above, in the presence of oxygen and a catalyst, the improvement which consists in using, as catalyst, copper, copper oxide, a salt of copper with an inorganic acid, a carboxylic acid, or a sulphonic acid, or a copper β-diketonate chelate.

6. The improvement of claim 1, in which $R_1$ and $R_2$ together form a radical of formula —CH=CH—CH=CH—.

7. The improvement of claim 1, in which the compound of formula V is cyclohexylamine, morpholine or t-butylamine.

8. The improvement of claim 1, in which the catalyst is copper or a cuprous or cupric oxide, chloride, bromide, iodide, sulphate, nitrate, phosphate, borate, sulphide, thiosulphate, cyanide, cuprocyanide, thiocyanate, formate, acetate, propionate, butyrate, pentanoate, oxalate, resinate, naphthenate, benzene-carboxylate, or salicylate.

9. The improvement of claim 1, in which the reaction temperature is between 0° and 200° C., and the oxygen partial pressure is between 0.1 and 30 bars.

10. The improvement of claim 1, in which the reaction is effected in water or in an organic solvent.

11. The improvement of claim 1, in which an excess of the compound of formula V reacted with the 2-mercapto-thiazole or 2,2'-dithiazolyl disulphide is used as the solvent.

12. The improvement of claim 1, in which the ratio of the number of gram atoms of copper to the number of mols of 2-mercapto-thiazole or 2,2'-dithiazolyl disulphide is between 0.0001 and 0.5.

13. The improvement of claim 1, in which the reaction is stopped when an amount of oxygen substantially equivalent to the stiochiometric amount has been absorbed.

* * * * *